United States Patent
Wu et al.

(10) Patent No.: US 9,382,249 B2
(45) Date of Patent: Jul. 5, 2016

(54) ANTITUMOR AZA-BENZO [F] AZULEN DERIVATIVE, METHOD FOR PREPARING SAME, AND USE THEREOF

(71) Applicant: TIANYI BIOSCIENCE CO. LTD., Nanjing, Jiangsu (CN)

(72) Inventors: Xihan Wu, Jiangsu (CN); Liwu Fu, Jiangsu (CN); Dongmei Zhang, Jiangsu (CN); Yurong Wang, Jiangsu (CN)

(73) Assignee: TIANYI BIOSCIENCE CO., LTD. (CN)

( * ) Notice: Subject to any disclaimer, the term of this patent is extended or adjusted under 35 U.S.C. 154(b) by 100 days.

(21) Appl. No.: 14/380,596

(22) PCT Filed: Jan. 24, 2013

(86) PCT No.: PCT/CN2013/070919
§ 371 (c)(1),
(2) Date: Aug. 22, 2014

(87) PCT Pub. No.: WO2013/123840
PCT Pub. Date: Aug. 29, 2013

(65) Prior Publication Data
US 2015/0011536 A1    Jan. 8, 2015

(30) Foreign Application Priority Data
Feb. 24, 2012 (CN) .......................... 2012 1 0043316

(51) Int. Cl.
*A61K 31/551* (2006.01)
*C07D 471/12* (2006.01)
*C07D 471/14* (2006.01)

(52) U.S. Cl.
CPC ................................... *C07D 471/14* (2013.01)

(58) Field of Classification Search
CPC ........................... A61K 31/551; C07D 471/12
USPC ........................................... 514/220; 540/557
See application file for complete search history.

(56) References Cited

FOREIGN PATENT DOCUMENTS

| | | | |
|---|---|---|---|
| CA | 2258053 | 12/1997 | ........... C07D 487/04 |
| CN | 1227555 | 9/1999 | ........... C07D 255/04 |
| CN | 102603743 | 7/2012 | ........... A61K 31/551 |
| EP | 0934940 | 8/1999 | ........... C07D 487/04 |

OTHER PUBLICATIONS

International Search Report issued in corresponding application No. PCT/CN2013/070919, dated Apr. 25, 2013 (6 pgs).

*Primary Examiner* — Brenda Coleman
(74) *Attorney, Agent, or Firm* — Hayes Soloway P.C.

(57) ABSTRACT

The present invention relates to the field of pharmaceutical chemistry, and particularly to an aza-benzo[f]azulen derivative (I) and an antitumor effect thereof. Pharmacological tests show that the compound of the present invention has in vitro and in vivo antitumor activities, and can be developed into clinical drugs for treating or controlling diseases such as stomach cancer, lung cancer, liver cancer, breast cancer, colon cancer, prostate cancer, and oral cancer.

10 Claims, 3 Drawing Sheets

Days of tumor cell inoculation

Days of tumor cell inoculation

Days of tumor cell inoculation

ANTITUMOR AZA-BENZO [F] AZULEN DERIVATIVE, METHOD FOR PREPARING SAME, AND USE THEREOF

FIELD OF THE INVENTION

The present invention relates to the field of pharmaceutical chemistry, in particular to a class of aza-benzo [f] azulene derivatives (I) and antitumor effect thereof.

BACKGROUND OF THE INVENTION

Malignancies are seriously threat to people's health. According to WTO statistics, among over 5 billion people worldwide, on average up to 6.9 million people die each year from malignancies, there are also 8.7 million new cases, and this number is increasing every year. Therefore, research and development of antitumor drugs have already become an extremely challenging and significant part in the field of life science today. In recent years, with the rapid progress of life science research, basic processes such as signal transduction in various malignant cells, cell cycle regulation, induction of apoptosis, angiogenesis and cell-extracellular matrix interactions are being gradually clarified. As a result, the focus of today's research and development of antitumor drugs has shifted from traditional cytotoxic drugs with low selectivity and high toxicity to discovery of new antitumor drugs which have high efficiency, low toxicity and strong specificity, as well as selectively act on specific targets, using some of the key enzymes of cellular signal transduction pathway associated with tumor cell differentiation and proliferation as a drug target.

SUMMARY OF THE INVENTION

The present invention discloses a class of aza-benzo [f] azulene derivatives. Pharmacological tests show that the compounds of the invention have excellent antitumor effect.

Aza-benzo [f] azulene derivatives of the present invention have the following structural formula (I):

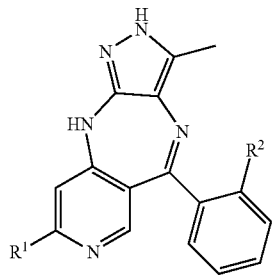

I wherein, $R^1$ represents C1-C6 hydrocarbon group, $R^2$ represents halogen.

$R^1$ preferably represents methyl or ethyl group.

$R^2$ preferably represents chloro or fluoro.

More preferred compound is as follows:

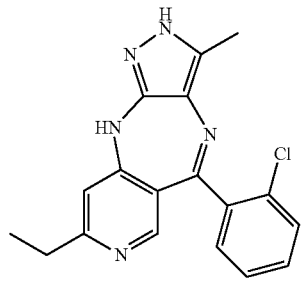 [SMILES: CCc1cc2c(cn1)C(c1ccccc1Cl)=Nc1c(n[nH]c1C)N2]

I-2

Compound I-2 is named as: 9-(2-chlorophenyl)-6-ethyl-1-methyl-2, 4-dihydrogen-2,3,4,7,10-pentaaza-benzo [f] azulene.

Compound (I) of the present invention can be combined with a pharmaceutically acceptable acid to yield a salt. Pharmaceutically acceptable salts may be in the form of an organic or inorganic acid. For example, salts may be formed by hydrochloric acid, sulfuric acid, phosphoric acid, maleic acid, fumaric acid, citric acid, methanesulfonic acid, toluenesulfonic acid or tartaric acid and similar known acceptable acids.

Compound (I) of the present invention may be prepared using the following method:

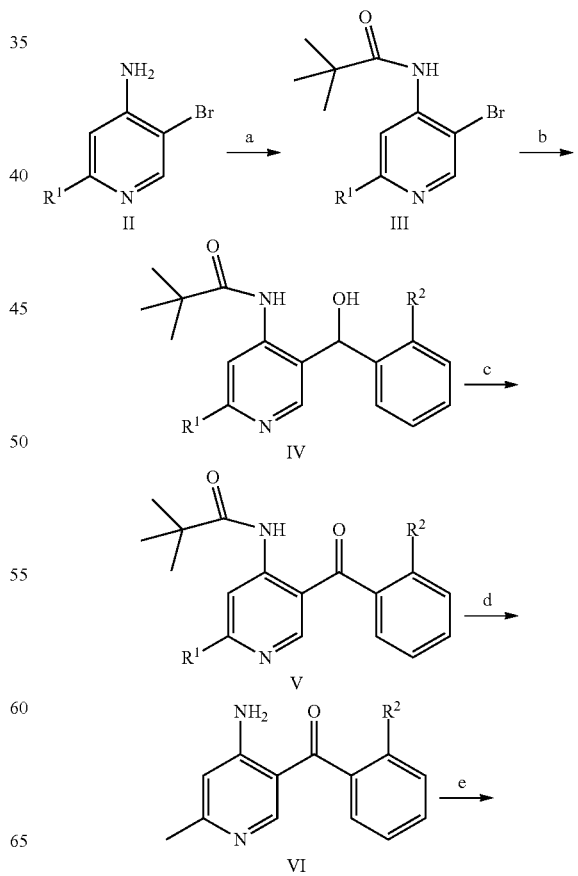

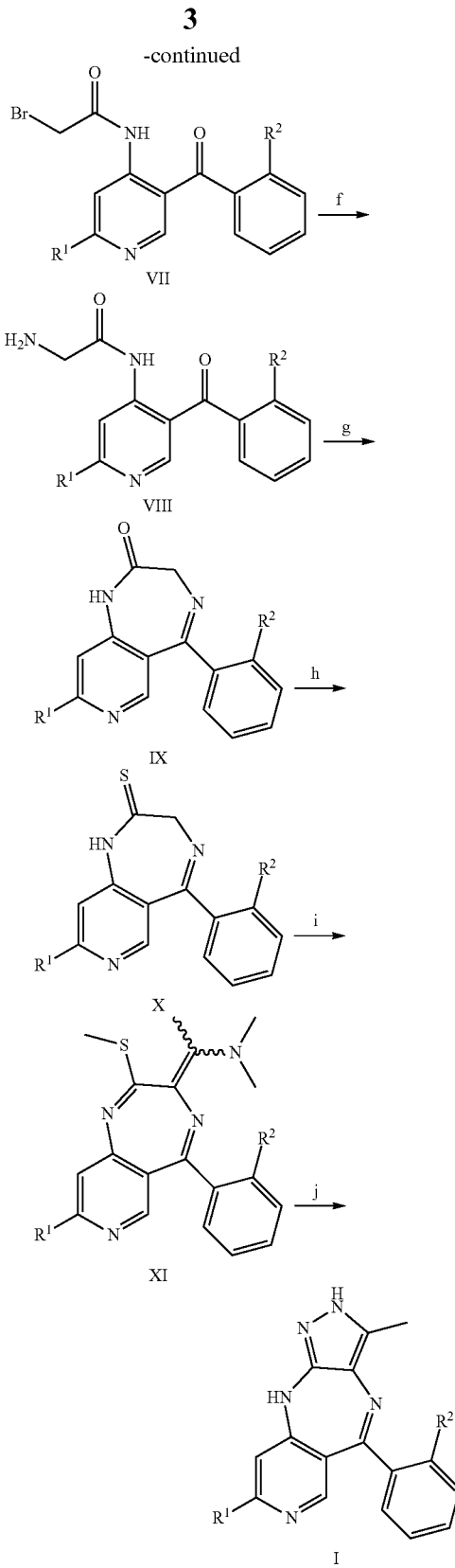

wherein, $R^1$ and $R^2$ are as previously defined.

The compound of the present invention may be prepared into common pharmaceutical preparations, such as tablets, capsules, powder, syrup, solution, suspension, and injection, by adding a pharmaceutically acceptable carrier, or adding common medicinal excipients, such as spice, sweeteners, liquid or solid fillers, or diluents, etc.

In clinical practice, the compound disclosed in the present invention may be administered orally, via injection, etc.

The compound of the present invention is administered clinically at a dose of 0.01 mg to 1000 mg/day, however, it may deviate from this range depending on the severity of the condition or dosage form.

Pharmacological tests show that the compounds of the invention have excellent antitumor activity, and its $IC_{50}$ value is in the range of 0.03 to 12.6 μM. Thus the compounds of the invention may be used for preparing drugs for the treatment of tumor diseases. The results of pharmacodynamic tests of some compounds of the present invention are as follows. Please see the structural formulas of compounds I-1 and I-3 in the embodiment.

I. An Evaluation of Growth Inhibition of Compounds I-1, I-2 and I-3 on Various Strains of Human Tumor Cell with MTT Assay Method: Cells in the logarithmic growth phase (human gastric cancer cell lines SGC-7901, MGC-803, human oral epidermoid carcinoma cell line KB, human non-small cell lung cancer cell line A549, human breast ductal cancer cell line BT-549, human prostate cancer cell line PC-3, human colon cancer cell line HT-29, human brain astrocytic glioblastoma cell line U-87MG and a human hepatoma cell line SMMC-7721) at a concentrations of $1.5 \times 10^4$ were inoculated in 96 well plates. The original medium was removed after cell culture for 24 hours until adherence. The tests included blank control group and drug treatment group. For the control group, the medium was replaced with 1640 medium containing 10% fetal bovine serum; for the drug treatment group, the medium was replaced with medium containing compounds I-1, I-2 and I-3 to be tested at concentrations of 100 μM, 50 μM, 10 μM, 1 μM, 0.1 μM, 0.01 μM, 0.001 μM, 0.0001 μM and 0.00001 μM. After incubation for 96 hours add MTT at a concentration of 5 mg/mL, and resume incubation in a $CO_2$ incubator for 4 hours. And then along the upper part of the culture solution, remove 100 μL, of supernatant, add 100 μL of DMSO, allow to place at a dark for 10 minutes. With a microplate reader (a product from Sunrise company), absorbance was measured (at wavelength 570 nm), and cell survival situation is calculated based on the absorbance. Six duplicated wells were set for each treatment. Cell viability (%)=$\Delta OD_{drug\ treatment}/\Delta OD_{blank\ control} \times 100$.

Results: Three compounds showed certain inhibitory effect on the growth of a variety of human tumor cell lines, wherein compounds I-1 and I-2 had a very significant inhibition. $IC_{50}$ value of these three compounds inhibiting growth of a variety of human tumor cell lines was calculated using Sigmaplot 10.0 software (see Table 1).

TABLE 1

$IC_{50}$ value of three compounds on a variety of human tumor cell lines

| | IC50 ± SD (μM) | | |
|---|---|---|---|
| Cell lines | I-1 | I-2 | I-3 |
| SGC-7901 | 0.29 ± 0.13 | 0.09 ± 0.01 | 1.63 ± 0.13 |
| MGC-803 | 0.98 ± 0.04 | 0.70 ± 0.02 | 4.86 ± 0.39 |
| KB | 1.35 ± 0.05 | 0.62 ± 0.01 | 7.27 ± 0.59 |
| A549 | 0.69 ± 0.24 | 0.25 ± 0.14 | 3.25 ± 0.25 |
| BT-549 | 0.39 ± 0.23 | 0.07 ± 0.03 | 1.95 ± 0.23 |
| PC-3 | 1.90 ± 0.39 | 0.85 ± 0.10 | 11.3 ± 1.30 |
| HT-29 | 0.16 ± 0.04 | 0.08 ± 0.01 | 0.74 ± 0.08 |
| U-89MG | 0.4 ± 0.02 | 0.06 ± 0.04 | 1.94 ± 0.24 |

TABLE 1-continued

IC$_{50}$ value of three compounds on a variety of human tumor cell lines

| Cell lines | IC50 ± SD (μM) | | |
|---|---|---|---|
| | I-1 | I-2 | I-3 |
| SMMC-7721 | 0.14 ± 0.03 | 0.04 ± 0.01 | 0.82 ± 0.19 |

II. In Vivo Animal Experiments Verifying Inhibition Effect of Compounds of the Present Invention on Growth of Human Gastric Cancer SGC-7901 Tumor Transplanted in Nude Mice Method: 1. Establishing model of human gastric cancer SGC-7901 tumor transplanted in nude mice, and animal groups: SGC_7901 cell lines were cultured with medium RPMI1640 containing 10% fetal bovine serum. SGC-7901 cells at logarithmic growth phase were trypsinized into single cell suspension. Final concentration of the cell was adjusted with medium RPMI1640 into 5×10$^7$/mL. 0.2 mL of cell suspension was injected subcutaneously into right anterior axillary of each nude mouse. 14 days after inoculation, when the tumor size grew to about 130 to 180 mm$^3$, the nude mice were randomized into five groups according to tumor size and body weight of mice, with 8-12 mice in each group. 5 groups were: a blank control group (purified water containing 0.5% of hydroxypropyl methylcellulose and 0.1% Tween 80, administered through gavage, each at morning and evening, for 10 days), 12.5, 25 and 50 mg/kg of I-1 treatment group (administered through gavage, each at morning and evening, for 10 days), and 100 mg/kg cyclophosphamide (CYP) group (by intraperitoneal injection, once every 5 days, for 2 weeks), respectively.

2. Growth situation of subcutaneous human gastric cancer tumor transplanted in nude mice and inhibitory effect was observed: from the dosing day, body weight of nude mouse as well as the maximum diameter (D) and minimum diameter (d) of tumor were observed every two days. The tumor size was calculated following the formula V=Dd$^2$/2, and the tumor growth curve was plotted. At the end of the experiment, the tumor was dissected in whole and picture was taken. Growth rate of nude mouse body weight before and after treatment= [(body weight after treatment−body weight before treatment)/body weight before treatment]*100%; tumor inhibition rate=[1−(tumor size after treatment in the experiment group−tumor size before treatment in the experiment group)/(tumor size after treatment in the control group−tumor size before treatment in the control group)]*100%

Results: It can be seen from FIG. 1 and FIG. 2 that the compound I-1 had higher inhibition on growth of human gastric cancer cell SGC-7901 tumor transplanted in nude mouse. In I-1 treatment group, growth of transplanted tumor was significantly inhibited, especially in the group receiving the highest dose. Final tumor growth inhibition rate in the 12.5, 25 and 50 mg/kg I-1 treatment groups reached 67.5%, 83% and 88.6%, respectively (see Table 2). It can be seen from FIG. 3 that the compound I-1 had mild effect on weight gain of nuke mouse only for the highest dose of 50 mg/kg, indicating compound I-1 had negligible toxic side effect and high safety, and potential value to be developed into an antitumor drug.

TABLE 2

Tumor inhibition rate among mice after treatment in each group

| Groups | Number of mice in each group | Dose | Inhibition rate (%) | P value |
|---|---|---|---|---|
| Blank control group | 12 | — | — | — |
| CYP group | 8 | 100 mg/kg | 39.5 | 0.0395 |
| I-1 | 11 | 12.5 mg/kg | 67.5 | 0.0053 |
| I-1 | 10 | 25 mg/kg | 83.0 | 0.0015 |
| I-1 | 10 | 50 mg/kg | 88.6 | 0.0008 |

III. In Vivo Animal Experiments Verifying Inhibition Effect of Compounds of the Present Invention on Growth of Human Gastric Cancer MGC-803 Tumor Transplanted in Nude Mice Method: 1. Establishing model of human gastric cancer MGC-803 tumor transplanted in nude mice, and animal groups: MGC-803 cell lines were cultured with medium RPMI1640 containing 10% fetal bovine serum. MGC-803 cells at logarithmic growth phase were trypsinized into single cell suspension. Final concentration of the cell was adjusted with medium RPMI1640 into 5×10$^7$/mL. 0.2 mL of cell suspension was injected subcutaneously into right anterior axillary of each nude mouse. 8 days after inoculation, when the tumor size grew to about 110 mm$^3$, the mice were randomized into five groups according to tumor size and body weight of mice, with 10 mice in each group. 5 groups were: a blank control group (purified water containing 0.5% of hydroxypropyl methylcellulose and 0.1% Tween 80, administered through gavage, once per day, for 10 days), 4, 6 and 9 mg/kg of I-2 treatment group (administered through gavage, once per day, for 17 days), and 100 mg/kg cyclophosphamide group (by intraperitoneal injection, once every 7 days, for 3 weeks), respectively.

2. Growth situation of subcutaneous human gastric cancer tumor transplanted in nude mice and inhibitory effect was observed: from the dosing day, body weight of nude mouse as well as the maximum diameter (D) and minimum diameter (d) of tumor were observed every 3-4 days. The tumor size was calculated following the formula V=Dd$^2$/2, and the tumor growth curve was plotted. At the end of the experiment, the tumor was dissected in whole and picture was taken. Growth rate of nude mouse body weight before and after treatment= [(body weight after treatment−body weight before treatment)/body weight before treatment]*100%; tumor inhibition rate=[1−(tumor size after treatment in the experiment group−tumor size before treatment in the experiment group)/(tumor size after treatment in the control group−tumor size before treatment in the control group)]*100%

Results: It can be seen from FIG. 4 and FIG. 5 that the compound I-2 had excellent inhibition on growth of human gastric cancer cell MGC-803 tumor transplanted in nude mouse. It can be seen from Table 3 that growth of human gastric cancer transplanted tumor was significantly inhibited in the compound I-2 treatment group, and final tumor inhibition rate in the 4, 6 and 9 mg/kg of I-2 treatment groups reached 72.5%, 97.3% and 100%, respectively. It can be seen from FIG. 6 that the compound I-2 had mild effect on weight gain of nuke mouse only for the group receiving the highest dose of 9 mg/kg on treatment day 3-6, indicating compound I-2 had negligible toxic side effect and high safety, and potential value to be developed into an antitumor drug with high efficiency and low toxicity.

TABLE 3

Tumor inhibition rate among mice after treatment in each group

| Groups | Number of mice in each group | Dose | Inhibition rate (%) | P value |
|---|---|---|---|---|
| Blank control group | 10 | — | — | — |
| CYP group | 10 | 100 mg/kg | 62.4 | 0.0017 |
| I-2 | 10 | 4 mg/kg | 72.5 | 0.0004 |
| I-2 | 10 | 6 mg/kg | 97.3 | 0.0000 |
| I-2 | 10 | 9 mg/kg | 100 | 0.0000 |

Tests mentioned above showed that the compounds of the present invention had a significant anti-proliferative activity against various human tumor cell lines. Animal experiment showed that the compounds I-2 had not only high in vivo tumor growth inhibition activity, but also negligible toxic side effect and high safety. These experiment results indicated that the compounds of this invention are useful for treating cancer, particularly the treatment of solid tumors, such as gastric cancer, lung cancer, liver cancer, breast cancer, colon cancer, prostate cancer, oral cancer, and other diseases.

DETAILED DESCRIPTION OF THE EMBODIMENTS

Embodiment 1

Preparation of Compound I-1

Synthesis of Compound III-1

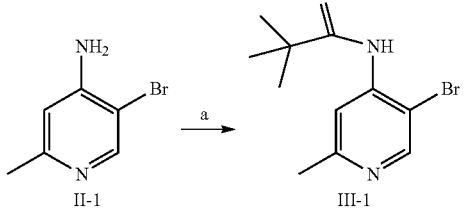

Figure 1:
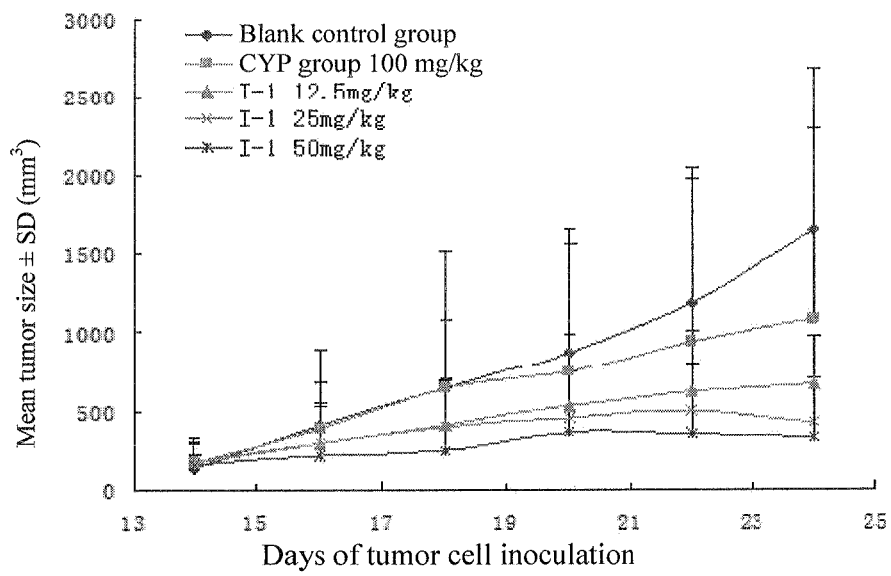
FIG. 1 shows the effect of compounds I-1 on growth of human gastric cancer SGC-7901 transplanted tumor
Figure 2:
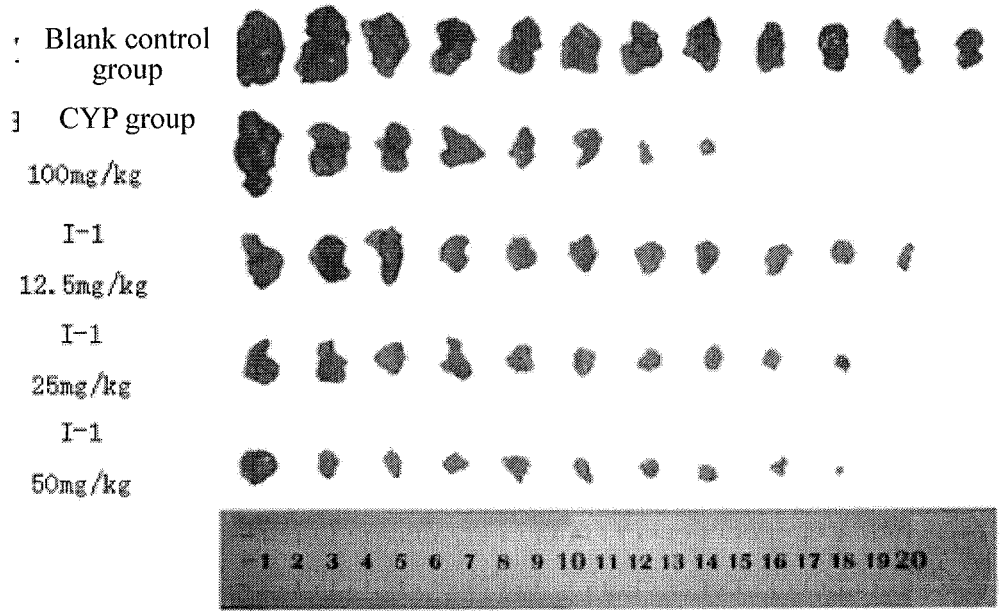
FIG. 2 shows tumor sizes of human gastric cancer SGC-7901 transplanted tumor in five groups after treatment
Figure 3:
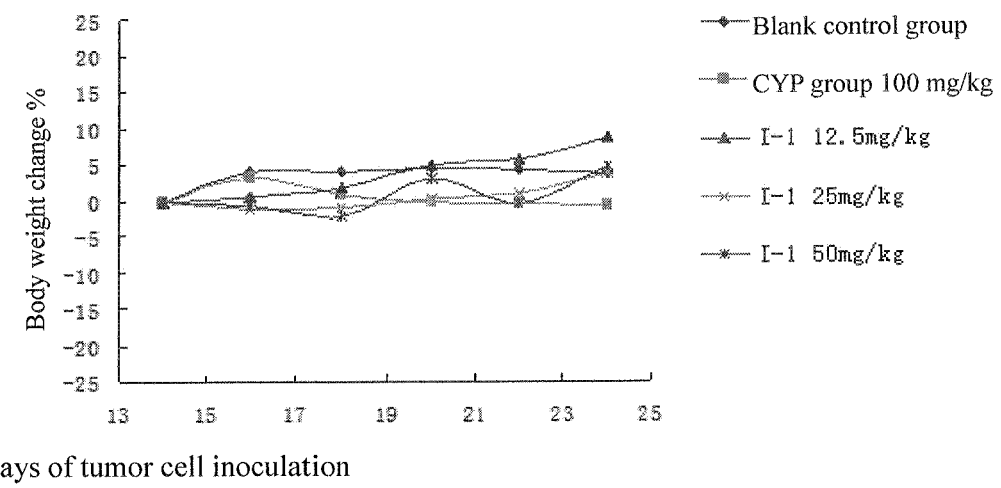
FIG. 3 shows body weight change of nuke mice in each group after drug treatment
Figure 4:
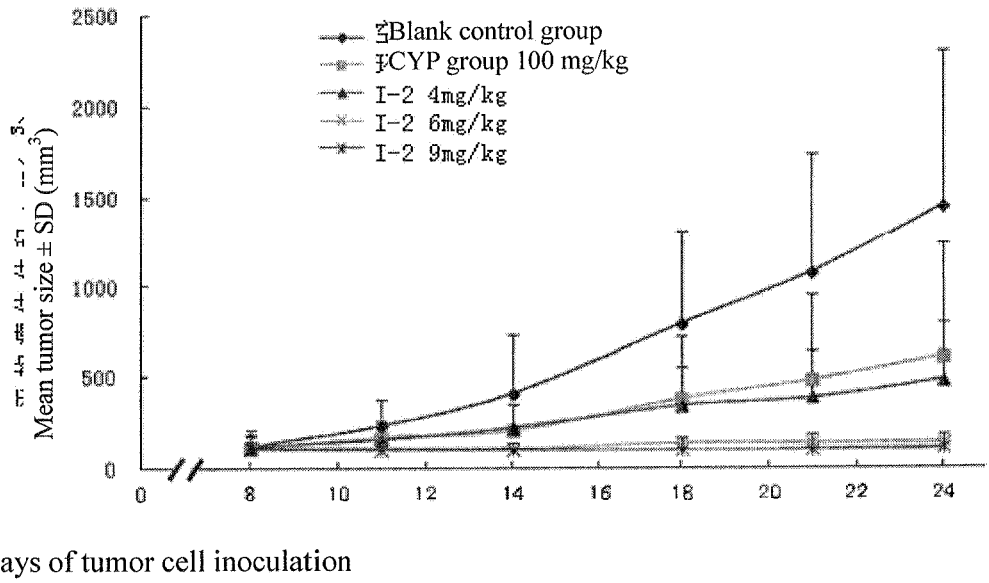
FIG. 4 shows the effect of compounds I-2 on growth of human gastric cancer MGC-803 transplanted tumor
Figure 5:
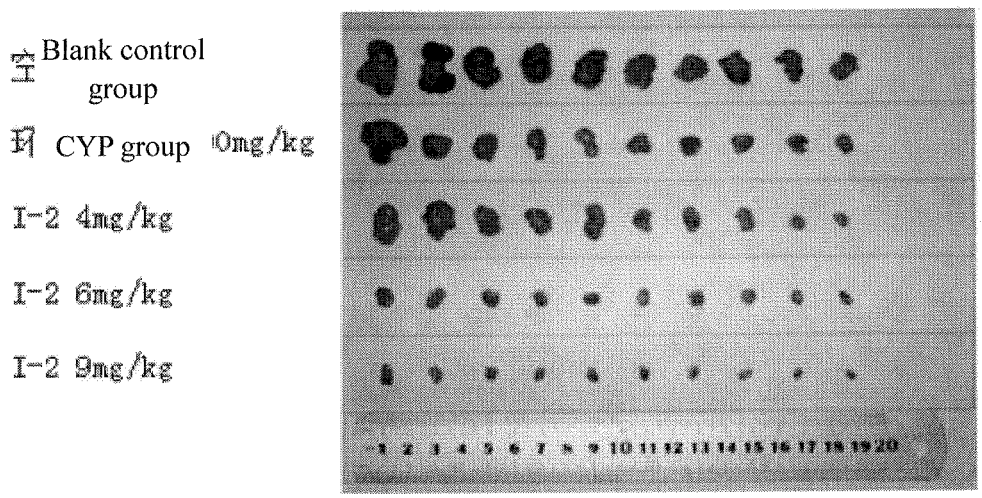
FIG. 5 shows tumor sizes of human gastric cancer MGC-803 transplanted tumor in five groups after treatment
Figure 6:
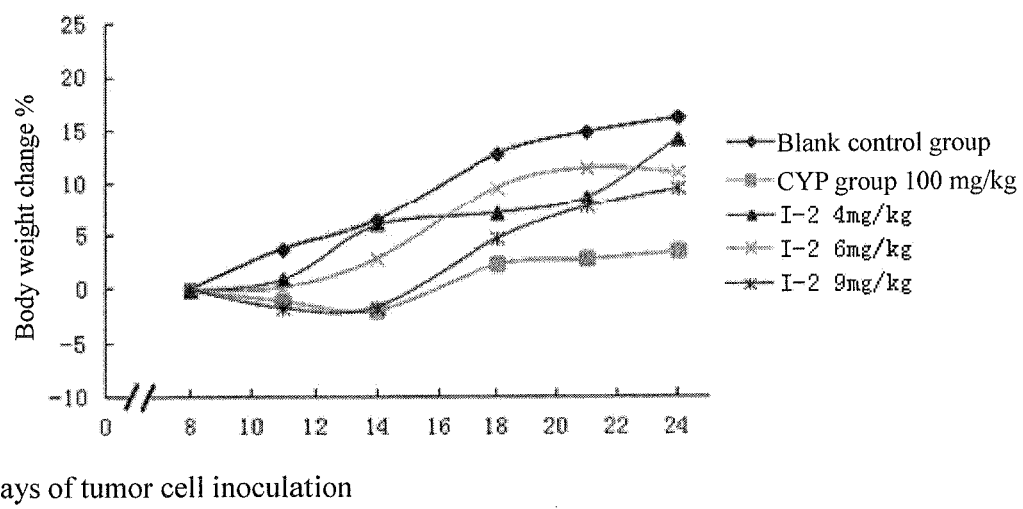
FIG. 6 shows body weight change of nuke mice in each group after drug treatment

Triethylamine (Et₃N) (56 g, 553.5 mmol, 1.5 eq.) is added into compound II-1 (69 g, 369 mmol, 1.0 eq.) in dichloromethane (DCM) (1 L) solution, then it is cooled to 0° C. To the resulting solution, add pivaloyl chloride (53.4 g, 442.8 mmol, 1.2 eq.) in DCM (170 mL) solution dropwise. Then it is heated to 15° C. The reaction is stirred for 10 hours. Then the reaction mixture is washed with water, saline, dried over anhydrous sodium sulfate, and concentrated, to afford 76 g of white solid of compound III-1, with a yield of 76.0%.

Synthesis of Compound IV-1

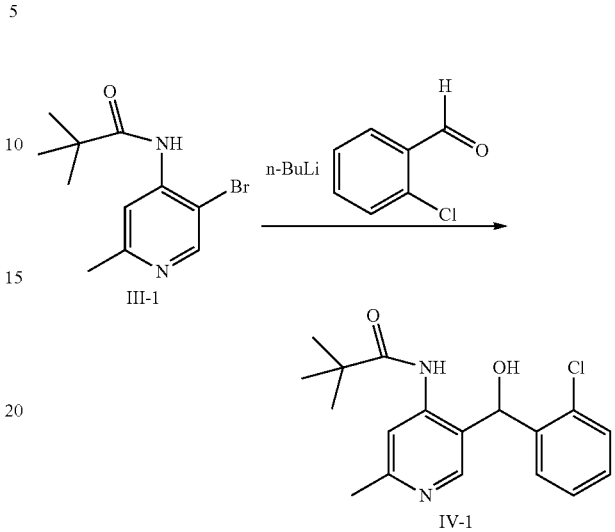

Under condition of $N_2$, at −78° C., n-BuLi (2.5 M of n-hexane solution) (300 mL, 0.75 mol, 3.0 eq.) is added into the compound III-1 (67.8 g, 0.25 mol, 1.0 eq.) and tetramethylethylenediamine (TMEDA) (87.15 g, 0.75 mol, 3.0 eq.) in THF (600 mL) solution dropwise. After that, reaction is stirred for 2 hours at −78° C. At −78° C., 2-chlorobenzaldehyde (70.28 g, 0.5 mol, 2.0 eq.) in tetrahydrofuran (THF) (200 mL) solution is added dropwise thereto. After the addition, further reaction is stirred for 4 hours at −78° C. $H_2O$ (20 mL) is slowly added at −78° C. dropwise thereto, and then it is heated to room temperature. Add ethyl acetate (EA), the organic phase is washed with water, and then saline. The organic phase is dried over anhydrous sodium sulfate, and concentrated. With petroleum ether (PE):EA=3:1 as the eluent, column chromatography is carried out to afford 70.0 g of white solid of compound IV-1, with a yield of 84.1%.

Synthesis of Compound V-1

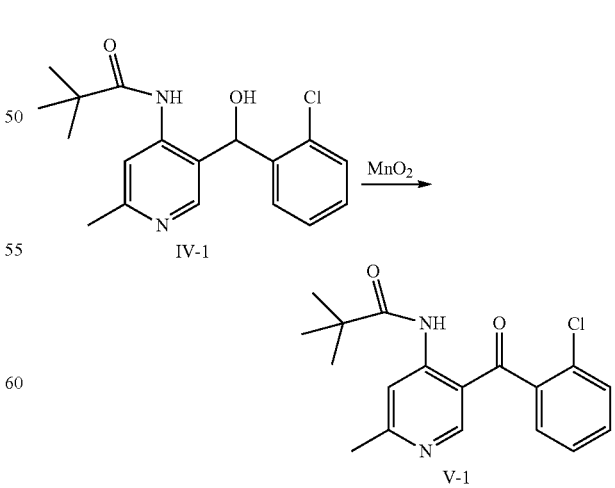

$MnO_2$ (127.9 g, 1.47 mol, 7.0 eq.) is added to compound IV-1 (70 g, 0.21 mol, 1.0 eq.) in EA (1300 mL) solution.

Under N$_2$ atmosphere, it is heated to reflux for 15 hours. Filter, and the filtrate is concentrated to afford 49.8 g of white solid of compound V-1, with a yield of 71.7%.

Synthesis of Compound VI-1

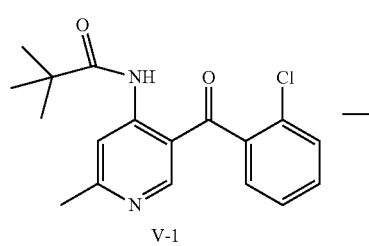

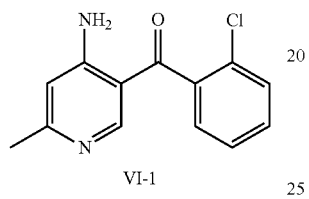

Compound V-1 (49.8 g, 0.15 mol, 1.0 eq.) is dissolved in methanol (MeOH) (1 L). Add 2 M of aqueous solution of NaOH (150 mL), and heat to reflux for 5 hours. Cool and concentrate to afford 35.4 g of white solid of compound VI-1. Yield: 95.6%.

Synthesis of Compound VII-1

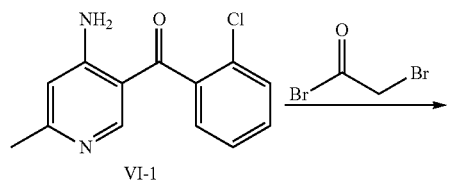

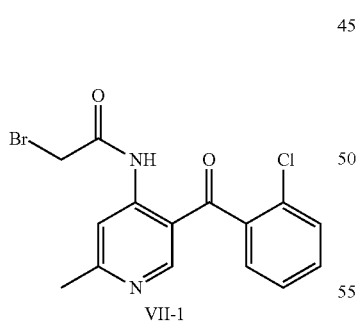

Et$_3$N (15.9 g, 0.157 mol, 1.1 eq.) is added into compound VI-1 (35.3 g, 0.143 mol, 1.0 eq.) in THF (500 mL) solution, then is cooled to 0° C. in an ice bath, and then bromoacetyl bromide (31.6 g, 0.157 mol, 1.1 eq.) is added dropwise thereto. After the addition, stir at room temperature for 5 hours. The reaction mixture is then poured into 100 ml, of ice water, and extracted with EA. After the organic phases are combined, washed with water and saline, dried over anhydrous sodium sulfate, and concentrated. Using PE:EA=2:1 column chromatography, to afford 34.2 g of pale yellow solid of compound VII-1, with a yield of 65.1%.

Synthesis of Compound VIII-1

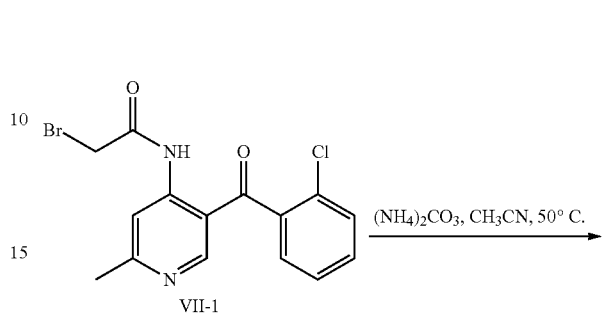

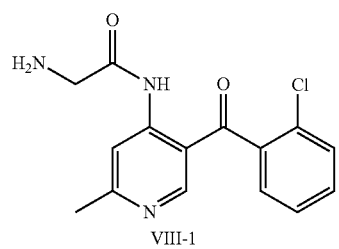

Compound VII-1 (14.8 g, 40.25 mmol, 1.0 eq.), (NH$_4$)$_2$CO$_3$ (30.9, 322 mmol, 8.0 eq.), and acetonitrile (1400 mL) are heated to 50° C., and allowed to react for 10 hours. Then it is cooled and filtered, and the filtrate is concentrated to afford 12.2 g of white solid of compound VIII-1, with a yield of 100%.

Synthesis of Compound IX-1

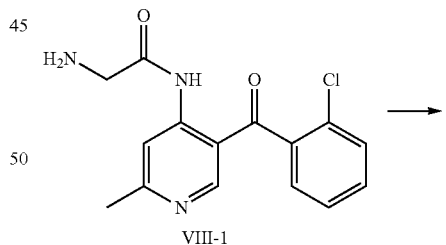

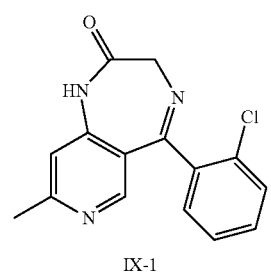

Compound VIII-1 (12.2 g, 40.25 mmol, 1.0 eq.) is added to ethanol (EtOH) (450 mL), and heated to reflux for 24 hours.

The crude product is concentrated, and recrystallized with PE/EA to afford 10.0 g of white solid of compound IX-1, with a yield of 87.0%.

Synthesis of Compound X-1

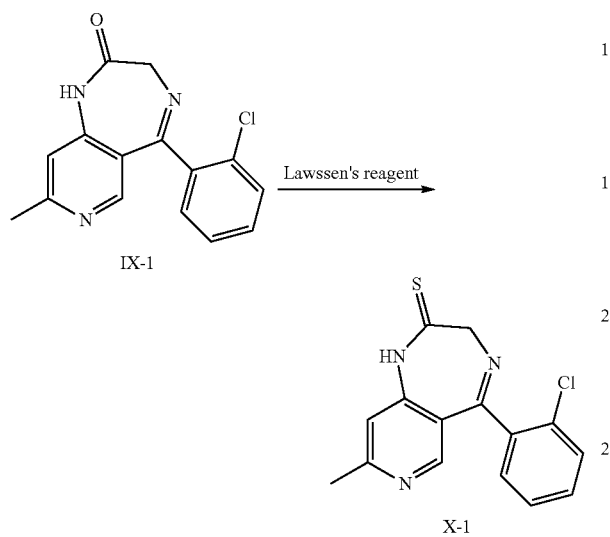

Compound IX-1 (12.0 g, 42 mmol, 1.0 eq.) and Lawesson's reagent (20.38 g, 50.4 mmol, 1.2 eq.) are added into dimethoxyethane (DME) (1200 mL), and heat to 85° C. and allow to react for 3 hours. The solvent is concentrated to a half and the residue is poured into a cold aqueous solution of $Na_2CO_3$. It is extracted with EA (300 mL×2) and organic phases are combined, washed with water and saline, dried over anhydrous sodium sulfate, and concentrated. The crude product obtained is recrystallized with EA to afford 8.31 g of pale yellow solid of compound X-1, with a yield of 65.5%.

Synthesis of Compound XI-1

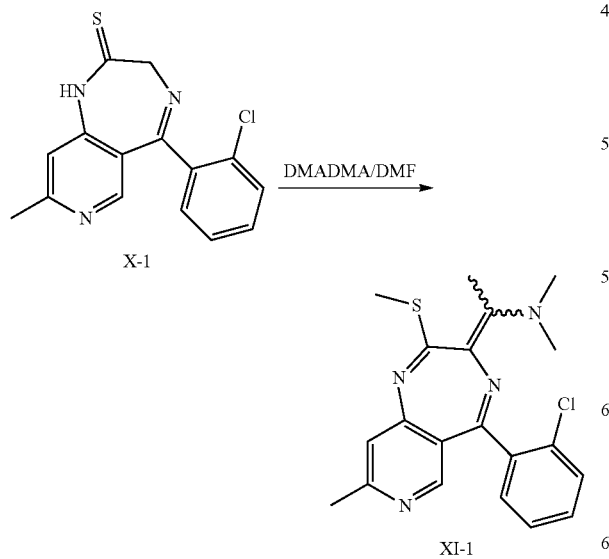

Compound X (4.27 g, 14.14 mmol, 1.0 eq.) and N,N-dimethylacetamide dimethylacetal (DMA-DMA) (7.53 g, 56.56 mmol, 4.0 eq.) are added into N,N-dimethylformamide (DMF) (60 mL). Stir at 20° C. for 2 hours, then heat to 110° C. and allow to react for 10 hours. It is concentrated to afford 4.57 g of red solid of compound XI-1, with a yield of 100%.

Synthesis of Compound I-1

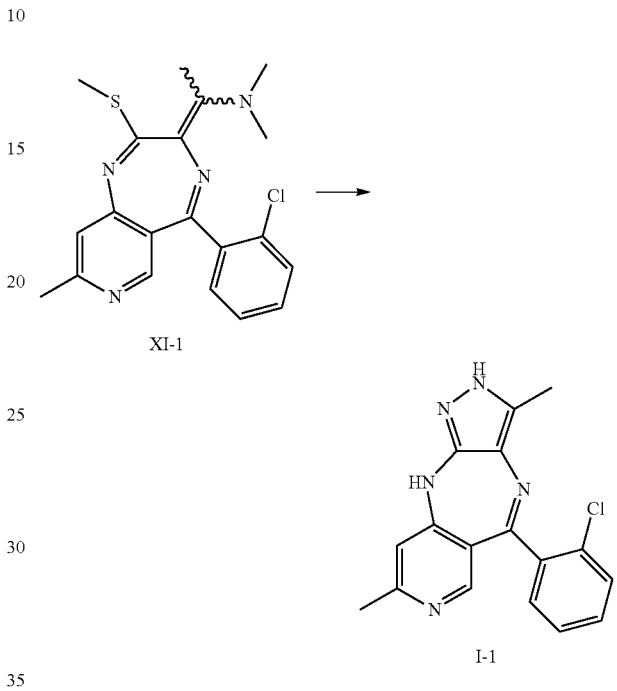

Compound XI-1 (4.57 g, 14.14 mmol, 1.0 eq.) and anhydrous hydrazinium (2.26 g, 70.7 mmol, 5.0 eq.) are added into MeOH (26 mL) and DCM (72 mL), and allowed to react at 20° C. for 24 hours. It is concentrated to afford the crude product, which is recrystallized with EA to afford 3.5 g of orange solid of compound I-1. Yield: 76.5%, purity: 99%.

$^1$HNMR (400 MHz, DMSO_d6) δ (ppm) 11.7 (s, 1H), 8.47 (s, 1H), 7.36-7.49 (m, 4H), 7.06 (s, 1H), 6.35 (s, 1H), 2.13 (s, 3H), 1.98 (s, 3H); MS (ES+APCI) M+1=324.

Embodiment 2

Preparation of Compound I-2

Synthesis of Compounds I-2

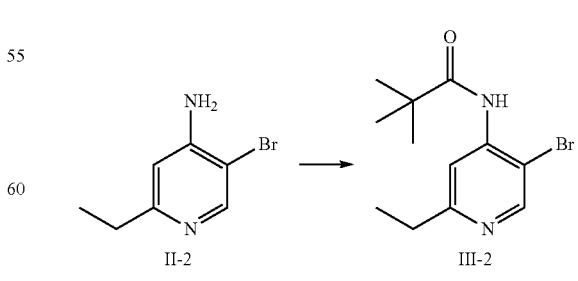

Compound II-2 (54.6 g, 272.9 mmol, 1.0 eq.) and $Et_3N$ (153.3 mL, 1.09 mol, 4.0 eq.) is added into 700 mL of DCM. In an ice-water bath, it is cooled to less than 5° C. Pivaloyl chloride (98.7 g, 818.7 mmol, 3.0 eq.) dissolved in 170 mL of DCM is added into the reaction mixture dropwise. After addition, the reaction solution is heated to room temperature and stirred for about 10 hours. Then the reaction solution is washed with water and saline, dried over anhydrous sodium sulfate, and concentrated to afford 58.1 g of white solid of compound III-2 58.1 g, with a yield of 74.7%. $^1$HNMR (400 MHz, CDCl$_3$) δ (ppm) 8.55 (s, 1H), 8.34 (s, 1H), 8.16 (br, 1H), 2.76-2.81 (q, J=7.56, 2H), 1.37 (s, 9H), 1.28-1.32 (t, J=7.56, 3H).

Synthesis of Compound IV-2

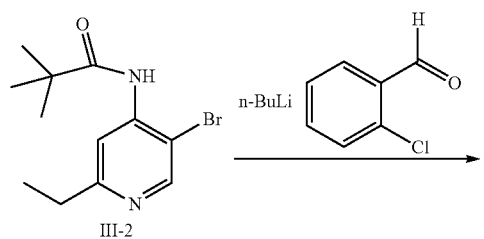

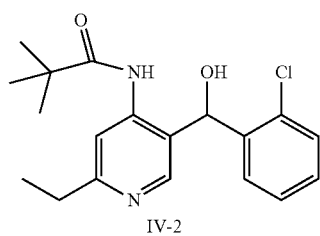

Under protection of N$_2$, compound III-2 (58.1 g, 203.7 mmol, 1.0 eq.) and TMEDA (71.0 g, 611.2 mmol, 3.0 eq.) are dissolved in 600 mL of THF. The reaction solution is cooled to −78° C. Add n-BuLi (2.5 M of n-hexane solution, 244.5 mL, 611.2 mmol, 3.0 eq.) dropwise. The reaction temperature is maintained below −78° C. After completion of addition, the reaction solution is allowed to continue reaction under stirring at −78° C. for 1 hour. Then, o-chlorobenzaldehyde (57.8 g, 407.4 mmol, 2.0 eq.) is dissolved in 200 mL of THF and added into the reaction solution dropwise. The reaction temperature is maintained below −78° C. After completion of addition, the reaction solution is allowed to continue reaction under stirring at −78° C. for 2.5 hours. After completion of the reaction, at −78° C., acetic acid (AcOH) (36.7 g, 611.2 mmol, 3.0 eq.) is added dropwise to quench the reaction. After the reaction solution is heated to room temperature, the reaction solution is diluted with water and EA. Organic phase is obtained by separating the mixture, and the aqueous phase is extracted with EA once. The organic phase is combined, washed once with saturated saline, and dried over anhydrous sodium sulfate. The organic phase is concentrated, and column chromatography (PE:EA=5:1-3:1) is carried out to afford 60.1 g of white solid of compound IV-2, with a yield of 85.2%. $^1$HNMR (400 MHz, CDCl$_3$) δ (ppm) 9.66 (br, 1H), 8.30 (s, 1H), 7.88 (s, 1H), 7.43 (d, J=7.76, 1H), 7.22-7.32 (m, 1H), 6.21 (s, 1H), 4.94 (br, 1H), 2.74-2.80 (q, J=7.56, 2H), 1.27 (s, 9H), 1.28-1.30 (t, J=7.56, 3H).

Synthesis of Compound V-2

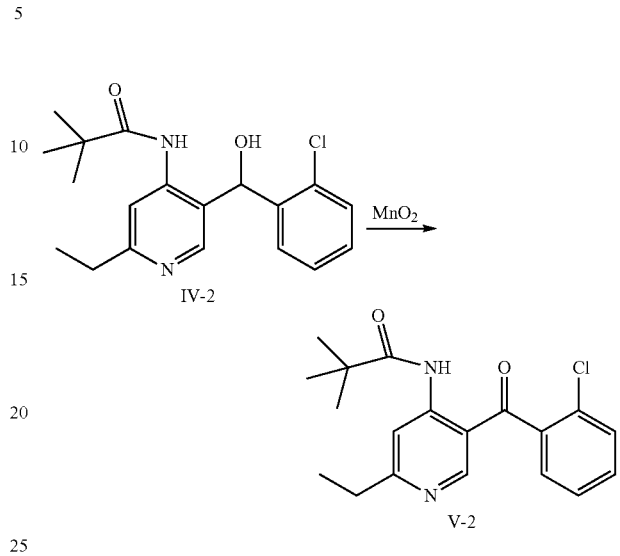

Compound IV-2 (22.3 g, 64.3 mmol, 1.0 eq.) is dissolved in 500 mL of EA, and then MnO$_2$ (55.9 g, 643.0 mmol, 10.0 eq.) is added once every half an hour, in total 10 times. After addition, the reaction solution is allowed to continue reaction under stirring at room temperature for 8 hours. The reaction is completed. The reaction solution is filtered and the filtrate is concentrated to dryness to afford 22.2 g of colorless oil of compound V-2, with a yield of 100.0%. $^1$HNMR (400 MHz, CDCl$_3$) δ (ppm) 11.95 (br, 1H), 8.68 (s, 1H), 8.47 (s, 1H), 7.46-7.52 (m, 2H), 7.36-7.44 (m, 2H), 2.83-2.89 (q, J=7.56, 2H), 1.38 (s, 9H), 1.32-1.36 (t, J=7.56, 3H).

Synthesis of Compound VI-2

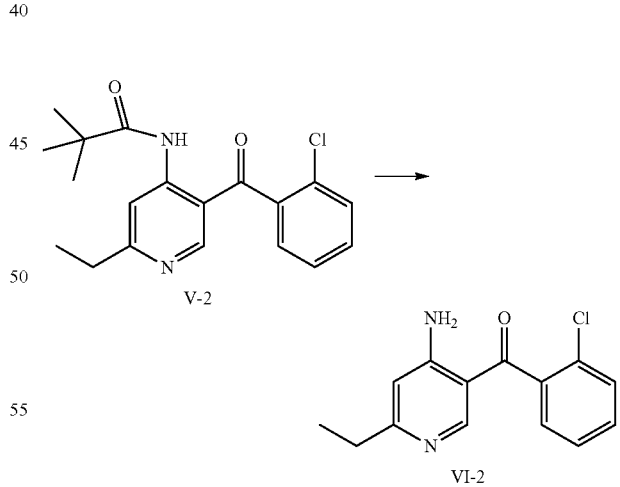

Compound V-2 (22.2 g, 64.3 mmol, 1.0 eq.) is dissolved in a mixed solvent of 1 N of aqueous solution of NaOH (140 mL, 2.0 eq.) and 500 mL of MeOH. The reaction solution is heated to reflux and allowed to react under stirring for 4 hours. When LC-MS detection material XV1-2 is disappeared, the reaction is completed. The reaction solution is concentrated and the residual water phase is extracted with EA several times. The organic phase is combined and washed with saturated saline once, dried over anhydrous sodium sulfate, and concentrated to afford 17.5 g of brown oil of compound VI-2, with a yield of 100.0%. $^1$HNMR (400 MHz, CDCl$_3$) δ (ppm) 8.24 (s, 1H), 7.33-7.49 (m, 4H), 6.46 (s, 1H), 2.69-2.74 (q, J=7.56, 2H), 1.60 (br, 2H), 1.29-1.31 (t, J=7.56, 3H).

Synthesis of Compound VII-2

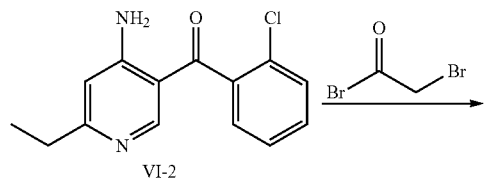

VI-2

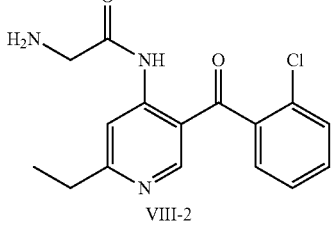

VIII-2

Compound VII-2 (14.0 g, 36.7 mmol, 1.0 eq.) is dissolved in 1400 mL of CH$_3$CN, and then (NH$_4$)$_2$CO$_3$ (35.2 g, 366.8 mmol, 8.0 eq.) is added. The reaction solution is allowed to react under stirring at room temperature overnight. After completion of the reaction, the reaction solution is filtered and the filtrate is concentrated to obtain 11.7 g of red oil of compound VIII-2, with a yield of 100%.

Synthesis of Compound IX-2

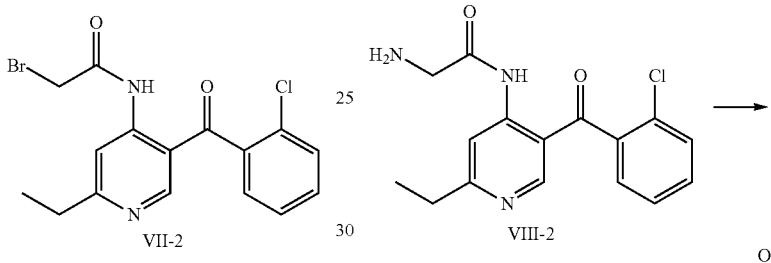

VII-2

Compound VI-2 (17.5 g, 67.1 mmol, 1.0 eq.) and Et$_3$N (15.9 g, 73.8 mmol, 1.1 eq.) are dissolved in 400 mL of THF, and the reaction solution is cooled to 0° C. Then bromoacetyl bromide (14.9 g, 73.8 mmol, eq.) is slowly added into the reaction solution dropwise. The temperature is maintained below 0° C. After completion of addition, the reaction solution is heated to room temperature and allowed to react under stirring overnight. After the reaction is complete, the reaction solution is poured into 100 g of ice-water, and the resulting mixed solution is separated to afford organic phase. The aqueous phase is extracted with EA. The organic phase is combined and washed with saturated saline once, dried over anhydrous sodium sulfate, and concentrated to give 16.5 g of yellow solid of compound VII-2, with a yield of 64.7%. $^1$HNMR (400 MHz, DMSO-d6) δ (ppm) 11.67 (br, 1H), 8.34 (s, 1H), 8.32 (s, 1H), 7.60-7.64 (m, 3H), 7.52-7.55 (m, 1H), 4.35 (s, 2H), 2.78-2.84 (q, J=7.56, 2H), 1.21-1.25 (t, J=7.56, 3H).

Compound VIII-2 (11.7 g, 36.7 mmol, 1.0 eq.) is dissolved in 200 mL of EtOH, and the solution is heated to reflux under stirring for about 3 hours. After the reaction is complete, the reaction solution is concentrated to give the crude product, which is recrystallized with PE and EA to afford 9.4 g of yellow solid of compound IX-2, with a yield of 85.4%. $^1$HNMR (400 MHz, CDCl$_3$) δ (ppm) 9.27 (br, 1H), 8.24 (s, 1H), 7.53-7.56 (m, 1H), 7.37-7.45 (m, 3H), 6.89 (s, 1H), 4.47 (s, 2H), 2.85-2.90 (q, J=7.56, 2H), 1.32-1.36 (t, J=7.56, 3H).

Synthesis of Compound X-2

Synthesis of Compound VIII-2

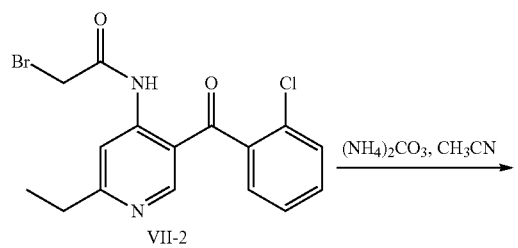

VII-2

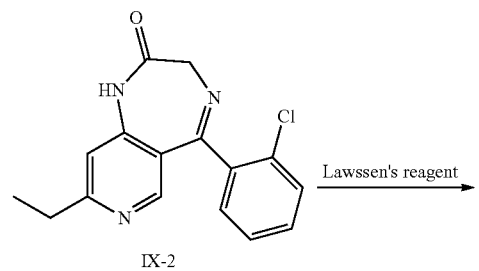

IX-2

-continued

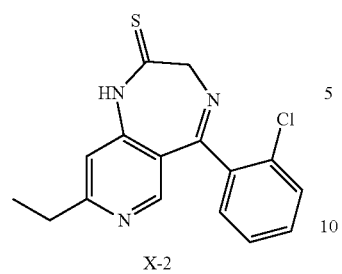

X-2

Compound IX-2 (5.0 g, 16.7 mmol, 1.0 eq.) is dissolved in 500 mL of DME, and then Lawesson's reagent (8.1 g, 20.0 mmol, 1.2 eq.) is added. The reaction solution is heated to reflux under stirring for about 3 hours. After completion of the reaction, the reaction solution is concentrated to remove half of the solvent, then the residual reaction solution is poured into icy, saturated aqueous solution of $Na_2CO_3$. The resulting aqueous phase is extracted with THF several times. The organic phase is combined and washed once with saturated saline, dried over anhydrous sodium sulfate, and concentrated to give the crude product. Then it is recrystallized with EA to afford 3.5 g of pale yellow solid of compound X-2, with a yield of 66.5%.

$^1$HNMR (400 MHz, CDCl$_3$) δ (ppm) 9.88 (br, 1H), 8.25 (s, 1H), 7.55-7.57 (m, 1H), 7.37-7.44 (m, 3H), 6.86 (s, 1H), 4.88 (s, 2H), 2.86-2.92 (q, J=7.56, 2H), 1.32-1.36 (t, J=7.56, 3H).

Synthesis of Compound XI-2

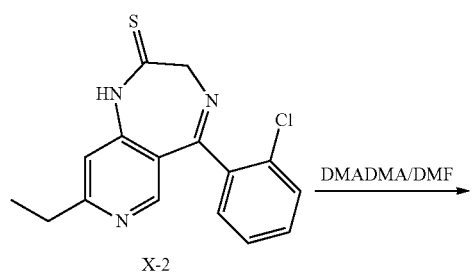

X-2 → DMADMA/DMF

Compound X-2 (4.1 g, 13.1 mmol, 1.0 eq.) and DMA-DMA (8.7 g, 65.5 mmol, 5.0 eq.) are dissolved in 85 mL of DMF. The reaction is stirred under room temperature for 2 hours, then heated to 80° C. and stirred overnight. The reaction solution is concentrated directly to dryness to afford 5.2 g of brown oil of crude compound XI-2, with a yield of 100%. It is to be used directly in the next step.

Synthesis of Compound I-2

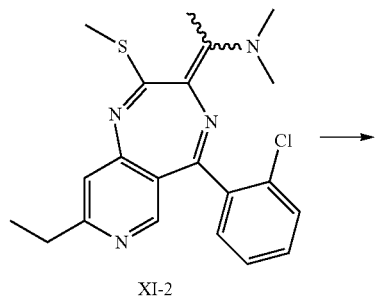

XI-2

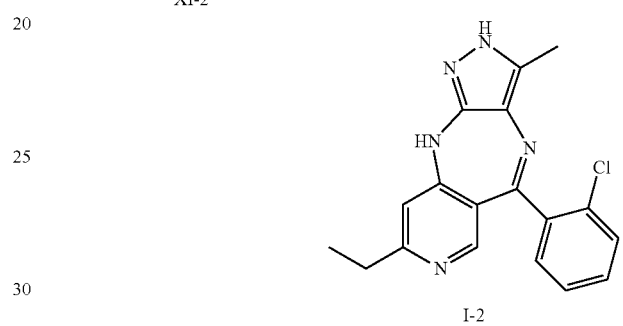

I-2

The compound XI-2 (5.2 g, 13.1 mmol, 1.0 eq.) and anhydrous hydrazinium (2.1 g, 65.5 mmol, 5.0 eq.) are dissolved in a mixed solvent of 60 mL of MeOH and 120 mL of DCM. The reaction solution is allowed to react at room temperature under stirring for 24 hours. The reaction solution is concentrated to give a crude product, which is then recrystallized by EA to afford 3.1 g of yellow solid of pure product I-2. Yield: 71.8%, purity: 98%.

$^1$HNMR (400 MHz, DMSO-d6) δ (ppm) 11.7 (br, 1H), 8.44 (s, 1H), 7.46-7.50 (m, 1H), 7.37-7.44 (m, 3H), 7.10 (s, 1H), 6.39 (s, 1H), 2.38-2.44 (q, J=7.56, 2H), 1.98 (s, 3H), 1.06-1.10 (t, J=7.56, 3H); MS (ES+APCI) M+1=338.

Embodiment 3

Preparation of Compound I-3

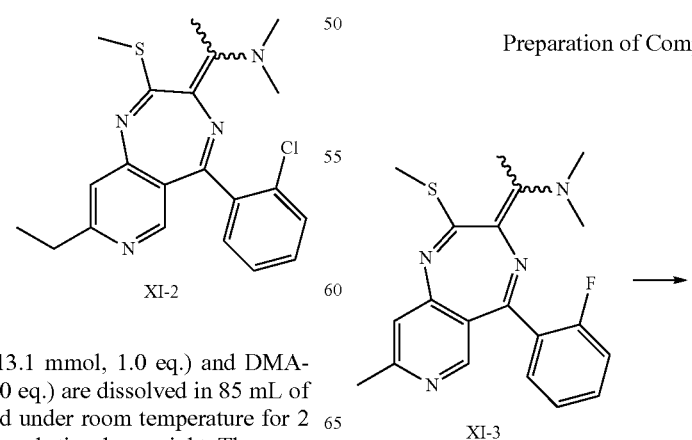

XI-3

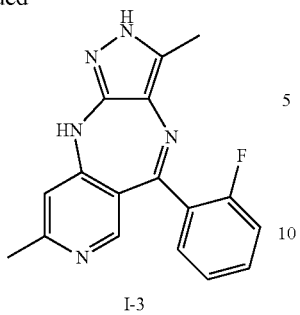

I-3

The specific synthesis method refers to Embodiment 1 and Embodiment 2.

$^1$HNMR (400 MHz, DMSO-d6) δ (ppm) 11.6 (s, 1H), 8.44 (s, 1H), 7.30-7.49 (m, 4H), 7.06 (s, 1H), 6.35 (s, 1H), 2.13 (s, 3H), 1.98 (s, 3H); MS (ES+APCI) M+1=308.

The invention claimed is:

1. Compound of structural formula (I) or a pharmaceutically acceptable salt thereof:

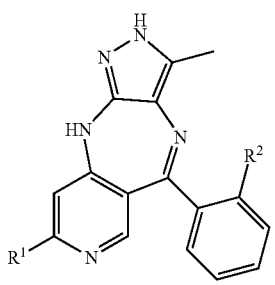

I wherein R$^1$ represents a C1-C6 alkyl group, R$^2$ represents halogen.

2. The compound or a pharmaceutically acceptable salt thereof according to claim 1, wherein R$^1$ represents a methyl or ethyl group.

3. The compound or a pharmaceutically acceptable salt thereof according to claim 1, wherein R$^2$ represents chloro or fluoro.

4. The compound or a pharmaceutically acceptable salt thereof according to claim 1, which is compound of the following structure or a pharmaceutically acceptable salts thereof:

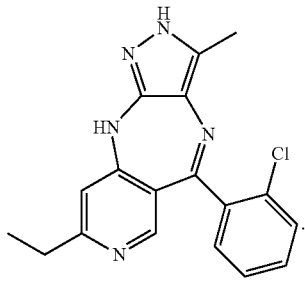 [SMILES: CCc1cc2c(cn1)C(c1ccccc1Cl)=Nc1c(n[nH]c1C)N2]

5. The compound or a pharmaceutically acceptable salt thereof according to claim 1, wherein the pharmaceutically acceptable salt is an arginine salt, hydrochloride, sulfate, phosphate, maleate, fumarate, citrate, methanesulfonate, p-toluenesulfonate, or tartrate of compound as claimed in claim 1.

6. A pharmaceutical composition comprising compound or a pharmaceutically acceptable salt thereof as claimed in claim 1 and a pharmaceutically acceptable carrier.

7. A method for treating cancer selected from the group consisting of gastric cancer, lung cancer, liver cancer, breast cancer, colon cancer, prostate cancer and oral cavity cancer, in an animal in need of treatment, which comprises administering to the animal a compound or a pharmaceutically acceptable salt thereof as claimed in claim 1.

8. The method according to claim 7, wherein the compound or pharmaceutically acceptable salt thereof is administered in a pharmaceutically acceptable carrier.

9. The method according to claim 7, wherein the cancer is gastric cancer.

10. The method according to claim 9, wherein the cancer is human gastric cancer.

* * * * *